(12) United States Patent
Shin et al.

(10) Patent No.: US 12,611,426 B2
(45) Date of Patent: Apr. 28, 2026

(54) ANTIBIOTIC COMPOSITION COMPRISING A COMPOSITE OF DIATOMACEOUS EARTH AND ZINC OXIDE, AND COMBINATION PREPARATION WITH THE SAME

(71) Applicant: UIF (University Industry Foundation), Yonsei University, Seoul (KR)

(72) Inventors: Yong Shin, Seoul (KR); Huifang Liu, Seoul (KR)

(73) Assignee: UIF (UNIVERSITY INDUSTRY FOUNDATION), YONSEI UNIVERSITY, Seoul (KR)

( * ) Notice: Subject to any disclaimer, the term of this patent is extended or adjusted under 35 U.S.C. 154(b) by 856 days.

(21) Appl. No.: 17/859,692

(22) Filed: Jul. 7, 2022

(65) Prior Publication Data

US 2023/0009330 A1 Jan. 12, 2023

(30) Foreign Application Priority Data

Jul. 9, 2021 (KR) ........................ 10-2021-0090180

(51) Int. Cl.
| | |
|---|---|
| A61K 33/30 | (2006.01) |
| A61K 9/14 | (2006.01) |
| A61K 31/496 | (2006.01) |
| A61K 31/7048 | (2006.01) |
| A01N 59/16 | (2006.01) |

(52) U.S. Cl.
CPC ................ *A61K 33/30* (2013.01); *A61K 9/14* (2013.01); *A61K 31/496* (2013.01); *A61K 31/7048* (2013.01); *A01N 59/16* (2013.01)

(58) Field of Classification Search
CPC ..................................................... A61K 33/30
See application file for complete search history.

(56) References Cited

U.S. PATENT DOCUMENTS

2017/0251674 A1* 9/2017 Naik ....................... A61P 31/04

FOREIGN PATENT DOCUMENTS

| | | | |
|---|---|---|---|
| KR | 10-2248492 B1 | | 5/2021 |
| KR | 10-2022-0145441 A | | 10/2022 |
| WO | WO2018031843 | * | 2/2018 |

OTHER PUBLICATIONS

Vedantu. Bacterial Diseases in Humans. Retrieved: (Year: 2025).*
Cleveland Clinic. Antivirals. Retrieved (Year: 2025).*
CDC. Risk Factors for Fungal Disease. Retrieved (Year: 2025).*

(Continued)

*Primary Examiner* — Sarah Alawadi
(74) *Attorney, Agent, or Firm* — Paratus Law Group, PLLC

(57) ABSTRACT

An antibiotic composition contains, as an active ingredient, a diatomaceous earth-zinc oxide composite comprising zinc oxide on diatomaceous earth, and an antifungal combination preparation contains a diatomaceous earth-zinc oxide composite including zinc oxide on diatomaceous earth and an antifungal agent. The antibiotic composition is less toxic while exhibiting excellent antibiotic activity, for example, antiviral, antibacterial or antifungal activity. The antibiotic composition is usable to prevent contamination or infection by viruses, bacteria or fungi, inhibit the growth of viruses, bacteria or fungi, or treat infections by viruses, bacteria or fungi.

15 Claims, 21 Drawing Sheets

(56)                References Cited

OTHER PUBLICATIONS

Sepsis Alliance. More about Viral Infections, prevention. Retrieved (Year: 2025).*

Rutherford. Growh Inhibition of Gram-Positive and Gram-Negative Bacteria by Zinc Oxide Hedgehog Particles. May 21, 2021.*

Kim et al. Preparation and Characterization of Positively Surface Charged Zinc Oxide Nanoparticles Against Bacterial Pathogens. May 2020.*

Butch KuKanic. A Review of Selected Systemic Antifungal Drugs for Use in Dogs and Cats. (Year: 2008).*

Healthline. (Necortizing Fascitis (Soft Tissue Inflammation). (Year: 2018).*

Korean Office Action for related KR Application No. 10-2021-0090180 mailed Jul. 3, 2023 from Korean Intellectual Property Office.

Aiping Hui et al., "Hydrothermal Fabrication of Spindle-Shaped ZnO/Palygorskite Nanocomposites Using Nonionic Surfactant for Enhancement of Antibacterial Activity", Nanomaterials, Oct. 13, 2019, pp. 1-13.

Sabriye Yusan et al., "Synthesis and structural properties of ZnO and diatomite-supported ZnO nanostructures", Ceramics International, Oct. 17, 2015, pp. 2158-2163, vol. 42.

Amna Sirelkhatim et al., "Review on Zinc Oxide Nanoparticles: Antibacterial Activity and Toxicity Mechanism", Nano-Micro Lett., Apr. 19, 2015, pp. 219-242.

* cited by examiner

ANTIBIOTIC COMPOSITION COMPRISING A COMPOSITE OF DIATOMACEOUS EARTH AND ZINC OXIDE, AND COMBINATION PREPARATION WITH THE SAME

CROSS-REFERENCE TO RELATED APPLICATION

This application claims priority to and the benefit of Korean Patent Application No. 10-2021-0090180, filed on Jul. 9, 2021, the disclosure of which is incorporated herein by reference in its entirety.

BACKGROUND

The present invention relates to an antibiotic composition including a composite of diatomaceous earth and zinc oxide and a combination preparation with the same.

Antibiotic resistance and antibiotic toxicity are major public health threats worldwide. In particular, infections caused by multi-drug resistant bacteria (super bacteria), fungi, gram-negative bacteria, or methicillin-resistant *S. aureus* (MRSA) are difficult to treat due to resistance to numerous antibiotics. Further, since mold infection weakens the patient's immune system, it causes increased mortality for cancer patients and organ transplant patients.

Among mold infections, invasive aspergillosis infection (IAI) is an infection with high mortality. Although examples of antifungal agents for treating *Aspergillus* infection include azole-based antifungal agents (for example, itraconazole), polyene-based antifungal agents (for example, amphotericin B), echinocandins and the like, their clinical use is extremely limited because these drugs have serious side effects such as nausea, diarrhea, abdominal pain, rashes, headaches, and organ damage.

Therefore, there is a need for the development of antibiotics capable of exhibiting improved efficacy while being less toxic.

SUMMARY

An object of the present invention is to provide a composition having low toxicity while exhibiting antiviral activity, antibacterial activity, or antifungal activity.

Another object of the present invention is to provide a composition which can be used in combination with existing antiviral, antibacterial or antifungal agents, may improve the efficacy of these antiviral, antibacterial or antifungal agents, and is less toxic.

According to an aspect of the present invention, provided is an antibiotic composition characterized by containing, as an active ingredient, a diatomaceous earth-zinc oxide composite including zinc oxide on diatomaceous earth.

According to another aspect of the present invention, provided is an antifungal combination preparation containing a diatomaceous earth-zinc oxide composite including zinc oxide on diatomaceous earth and an antifungal agent.

The antibiotic composition according to the invention is less toxic while exhibiting excellent antibiotic activity, for example, antiviral, antibacterial or antifungal activity. Accordingly, the antibiotic composition may be used to prevent contamination or infection by viruses, bacteria or fungi, inhibit the growth of viruses, bacteria or fungi, or treat infections by viruses, bacteria or fungi. In addition, when the antibiotic composition is used in combination with an existing antifungal agent, a synergistic effect is exhibited by improving the efficacy of the antifungal agent. Therefore, the antibiotic composition can be used as an excellent antifungal combination preparation, and enables the use of a low dose of an existing antifungal agent to reduce side effects due to toxicity.

DETAILED DESCRIPTION

Figure 1A:
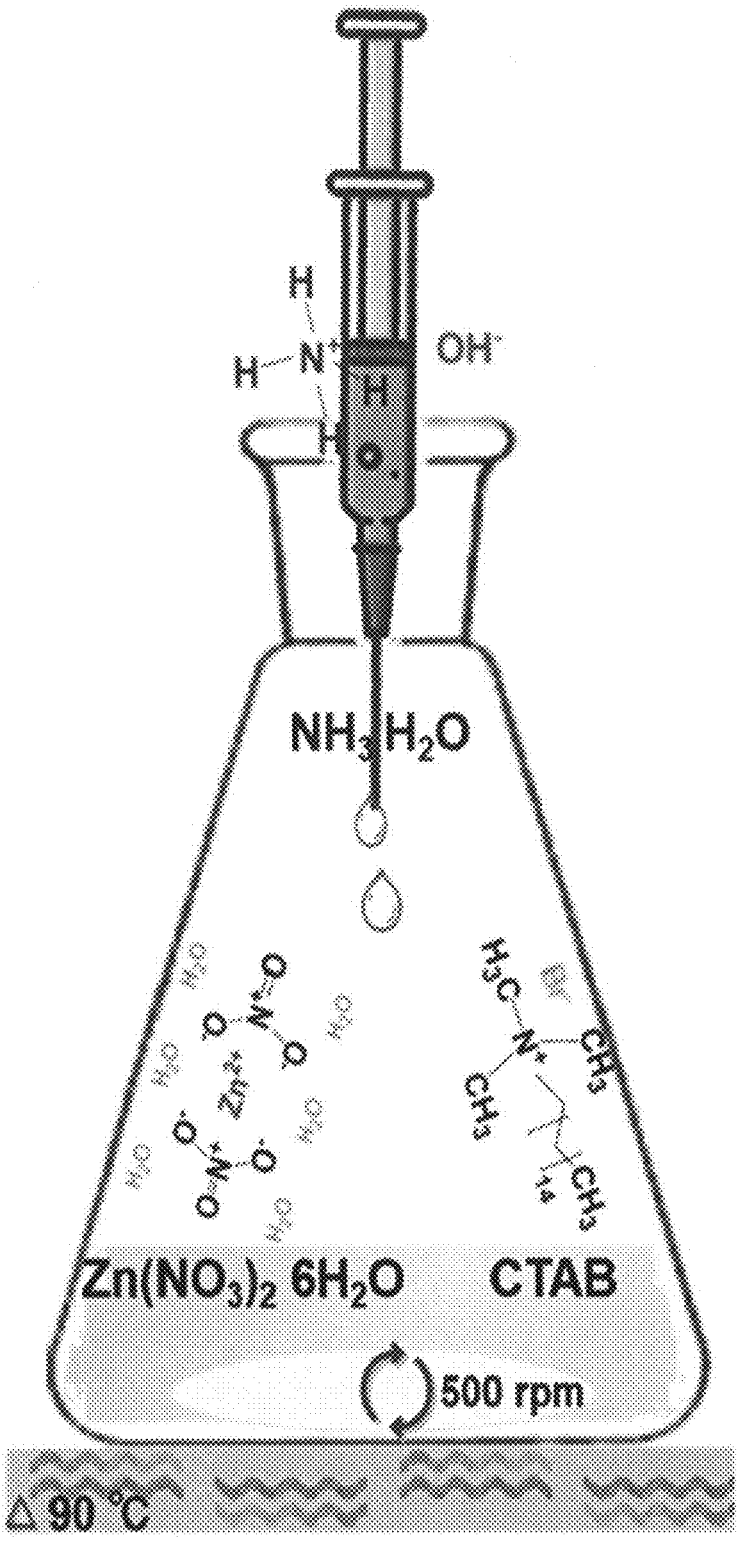
FIG. 1A is a view schematically illustrating a process of synthesizing a diatomaceous earth (DE)-zinc oxide (ZnO) composite according to an exemplary embodiment of the present invention.
Figure 1B:
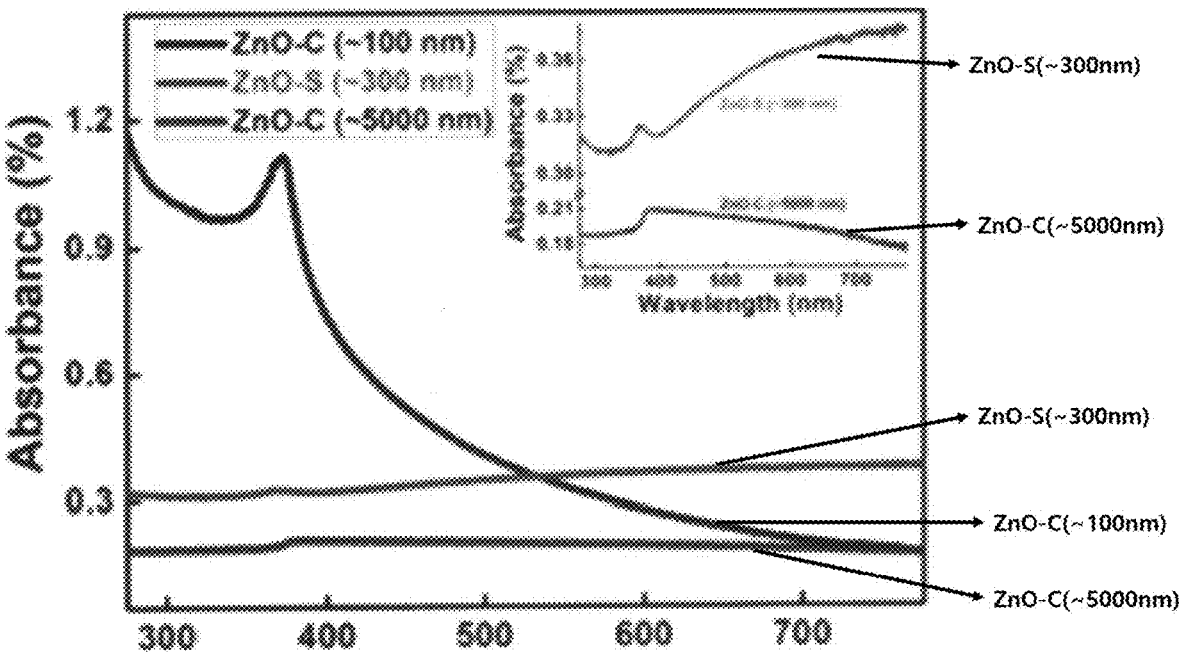
FIG. 1B is a UV-visible light absorption spectrum of a ZnO nanomaterial.
Figure 1C:
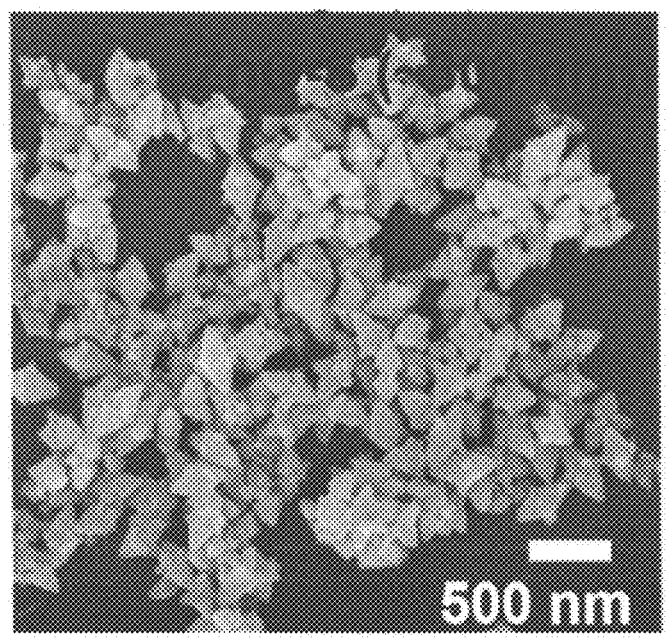
FIG. 1C is an SEM image of a synthesized ZnO nanomaterial.
Figure 1D:
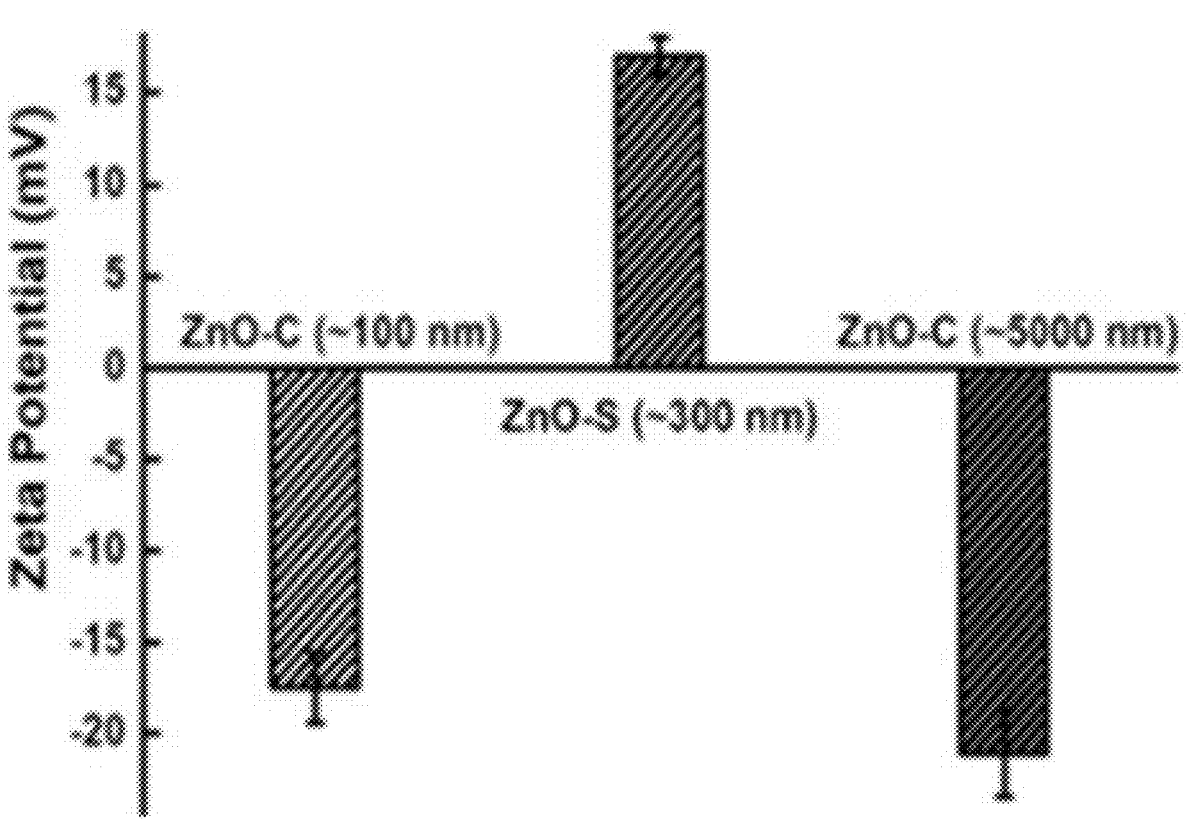
FIG. 1D is a graph showing the zeta potential of the synthesized ZnO nanomaterial.

Hereinafter, the present invention will be described in detail.

The terms used in the present application are used only to describe specific embodiments, and are not intended to limit the present invention. Unless defined otherwise, all terms used herein, including technical or scientific terms, have the same meaning as commonly understood by a person with ordinary skill in the art to which the present invention pertains.

Throughout the specification, when a part "includes", "contains" and "has" a constituent element, it means that other constituent elements may be further included unless otherwise specifically defined.

According to an aspect of the present invention, provided is an antibiotic composition characterized by containing, as an active ingredient, a diatomaceous earth-zinc oxide composite including zinc oxide on diatomaceous earth.

The diatomaceous earth is porous diatomaceous earth and serves as a matrix for zinc oxide. The diatomaceous earth is known to be non-toxic and is biocompatible. Although the diatomaceous earth exhibits a negative charge on the surface, the zinc oxide exhibits a positive surface charge because the surface is coated with cations (for example, $NH_4^+$) during synthesis and growth, whereby the diatomaceous earth-zinc oxide composite exhibits a positive surface charge. As the composite exhibits a positive charge as described above, it is possible to exhibit an effect of attracting microorganisms such as viruses, bacteria or fungi.

The zinc oxide may be in the form of nano-sized crystals. According to an exemplary embodiment of the present invention, the zinc oxide may be a nanocrystal having a diameter of 200 to 400 nm. Furthermore, according to an exemplary embodiment of the present invention, the zinc oxide may be a nanocrystal having at least one sharp protrusion shape, for example, a nanostar-shaped nanocrystal in which a plurality of sharp protrusions are arranged in an annular pattern. The sharp protrusions of zinc oxide as described above may help destroy the cell walls of microorganisms such as viruses, bacteria and fungi attracted by the positive surface charge. According to an exemplary embodiment of the present invention, the zinc oxide may be a nanocrystal synthesized and grown by hydrothermal synthesis on diatomaceous earth. The hydrothermal synthesis may be performed by heating a zinc precursor along with water at 85 to 95° C. for 30 to 80 minutes, and in this case, the zinc precursor may be heated along with a surfactant such as hexadecyltrimethylammonium bromide.

According to an exemplary embodiment of the present invention, the zinc oxide in the diatomaceous earth-zinc oxide composite may be included at a reaction ratio of 1 or more with respect to the diatomaceous earth. For example, the reaction ratio of zinc oxide to diatomaceous earth may be in a range of 1:1 to 4:1. Here, the larger the amount of zinc oxide, the better the antibiotic activity. In relation to the reaction ratio, the weight percentage of zinc oxide on diatomaceous earth may be, for example, approximately 2 to 2.1 wt %, approximately 4 to 5 wt %, 6 to 7 wt %, 10 to 11 wt %, 13 to 14 wt %, and 23 to 24 wt % when the reaction ratio of zinc oxide to diatomaceous earth is 0.25:1, 0.5:1, 1:1, 2:1, 3:1, and 4:1, respectively.

The antibiotic composition according to the present invention has antibiotic activity. As used herein, the term "antibiotic composition" refers to a composition containing antibiotics that kill microorganisms or suppress the growth of microorganisms, the microorganisms including viruses, fungi, protozoa and bacteria. Accordingly, the antibiotic has antibiotic activity, that is, antiviral activity, antibacterial activity, or antifungal activity. Thus, according to an exemplary embodiment of the present invention, the antibiotic composition of the present invention may be a composition having antiviral activity, antibacterial activity, or antifungal activity.

According to an exemplary embodiment of the present invention, the antibiotic composition according to the present invention may have antibacterial activity against Gram-negative bacteria. The composite according to the present invention is an ingredient effective for preventing bacterial contamination, inhibiting bacterial growth, or treating bacterial infection. Examples of the gram-negative bacteria include *Escherichia coli, Salmonella, Shigella,* Typhus, *Vibrio cholerae, Neisseria gonorrhoeae, Neisseria meningitidis,* and the like. According to an exemplary embodiment of the present invention, the composition of the present invention may have antibacterial activity against *Escherichia coli* or *Salmonella.*

According to an exemplary embodiment of the present invention, the antibiotic composition according to the present invention may have antifungal activity. The composite according to the present invention is an ingredient effective for preventing mold contamination, inhibiting mold growth, or treating mold infection. The composition having the antifungal activity according to the present invention may exhibit antifungal activity against pathogenic fungi, for example *Candida albicans, Cryptococcus neoformans, Candida glabrata, Candida lusitaniae, Candida tropicalis, Aspergillus niger, Aspergillus fumigatus, Fusarium oxysporum, Saccharomyces cerevisiae* and the like. According to an exemplary embodiment of the present invention, the composition of the present invention may have antifungal activity against fungi of the genus *Aspergillus.*

According to an exemplary embodiment of the present invention, the antibiotic composition according to the present invention may be used with an additional antifungal agent. Further, according to another aspect of the present invention, provided is an antifungal combination preparation containing a diatomaceous earth-zinc oxide composite including zinc oxide on diatomaceous earth and an antifungal agent. The antifungal agent used with the antibiotic composition according to the present invention or the antifungal agent included in the combination preparation along with the diatomaceous earth-zinc oxide composite may be, for example, one or more selected from the group consisting of ketoconazole, itraconazole, fluconazole, miconazole, clotrimazole, fenticonazole, econazole, bifonazole, oxiconazole, chloconazole, roll cyclate, amphotericin B, flucytosine, griseofulvin, terbinafine, nystatin, tolnaftate, naftifine, haloprogin, ciclopirox, triclosan, noprosacsin, ciprosacsin and salts. According to an exemplary embodiment of the present invention, the antifungal agent may be itraconazole or amphotericin B. Specifically, the antibiotic composition containing the diatomaceous earth-zinc oxide composite according to the present invention may be administered simultaneously or at different times from when itraconazole or amphotericin B is administered, or may be administered by formulating the diatomaceous earth-zinc oxide composite according to the present invention into a combination preparation with itraconazole or amphotericin B.

The method for administering the composition or combination preparation according to the present invention is not particularly limited, but the composition or combination preparation according to the present invention may be administered parenterally or orally, and accordingly, may be used in combination with a pharmaceutically acceptable carrier, excipient, diluent, or the like. Meanwhile, the composition according to the present invention does not necessarily need to be administered to humans or non-human animals, and may be combined with an appropriate diluent, and the like and thus used after being formulated into a form to be sprayed or applied to a required place or device for the purpose of preventing contamination by viruses, fungi or bacteria or inhibiting their reproduction.

Hereinafter, the present invention will be described in more detail with reference to exemplary embodiments of the present invention. Since the exemplary embodiments are presented for the purpose of describing the present invention, the present invention is not limited thereto.

SYNTHESIS EXAMPLES

(1) Synthesis of ZnO

As illustrated in FIG. 1A, 1 mL of 1 M hexadecyltrimethylammonium bromide (CTAB) was added to 98 mL of ultrapure water (Milli-Q water), and the resulting mixture was stirred at 90° C. to 500 rpm. Thereafter, 1 mL of 1 M $ZnNO_3 \cdot 6H_2O$ was added thereto, and the resulting mixture was additionally stirred for 50 minutes. 2 mL of an ammonium hydroxide solution was added dropwise thereto under constant-rate stirring and constant temperature incubation conditions. A white precipitate was formed and the reaction vessel was transferred to an ice bath to stop the reaction. The white precipitate was collected by centrifugation and washed 3 times with ultrapure water (Milli-Q water) to remove residual ions. Thereafter, the white precipitate was dried at 56° C. overnight. FIG. 1B is a UV-visible light absorption spectrum of a ZnO nanomaterial, and it was confirmed that ZnO was produced from the peak at 381 nm, which is a characteristic peak of ZnO. An SEM image of the white precipitate is illustrated in FIG. 1C, which is uniformly-sized ZnO—S (approximately 300 nm). In addition, referring to FIG. 1D, it was confirmed that ZnO—S was coated with $NH_4^+$ to generate a positive surface charge.

(2) Preparation of Diatomaceous Earth (DE)-Zinc Oxide (ZnO) Composite

Figure 2A:
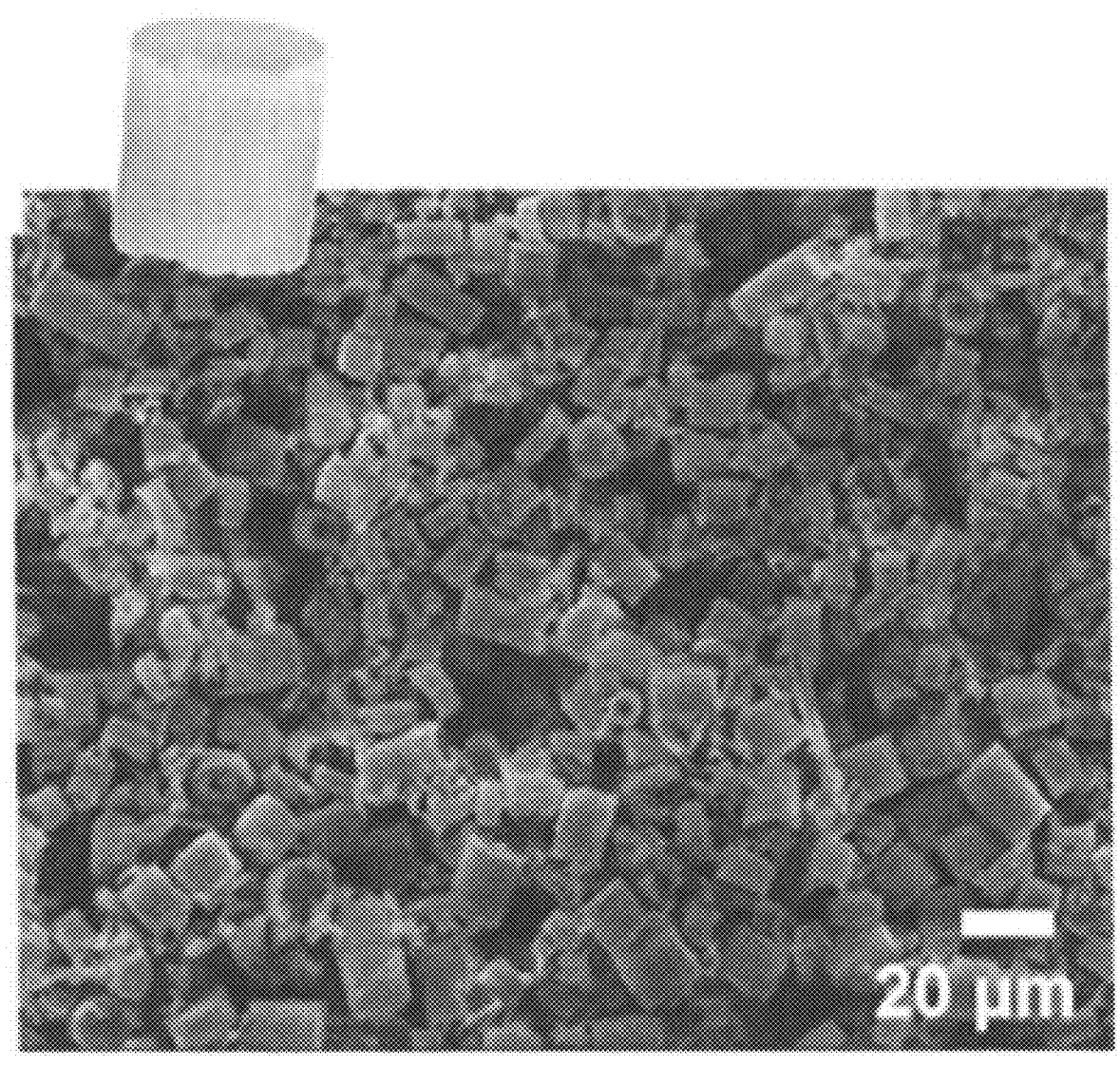
FIG. 2A is an SEM image of DE.
Figure 2B:
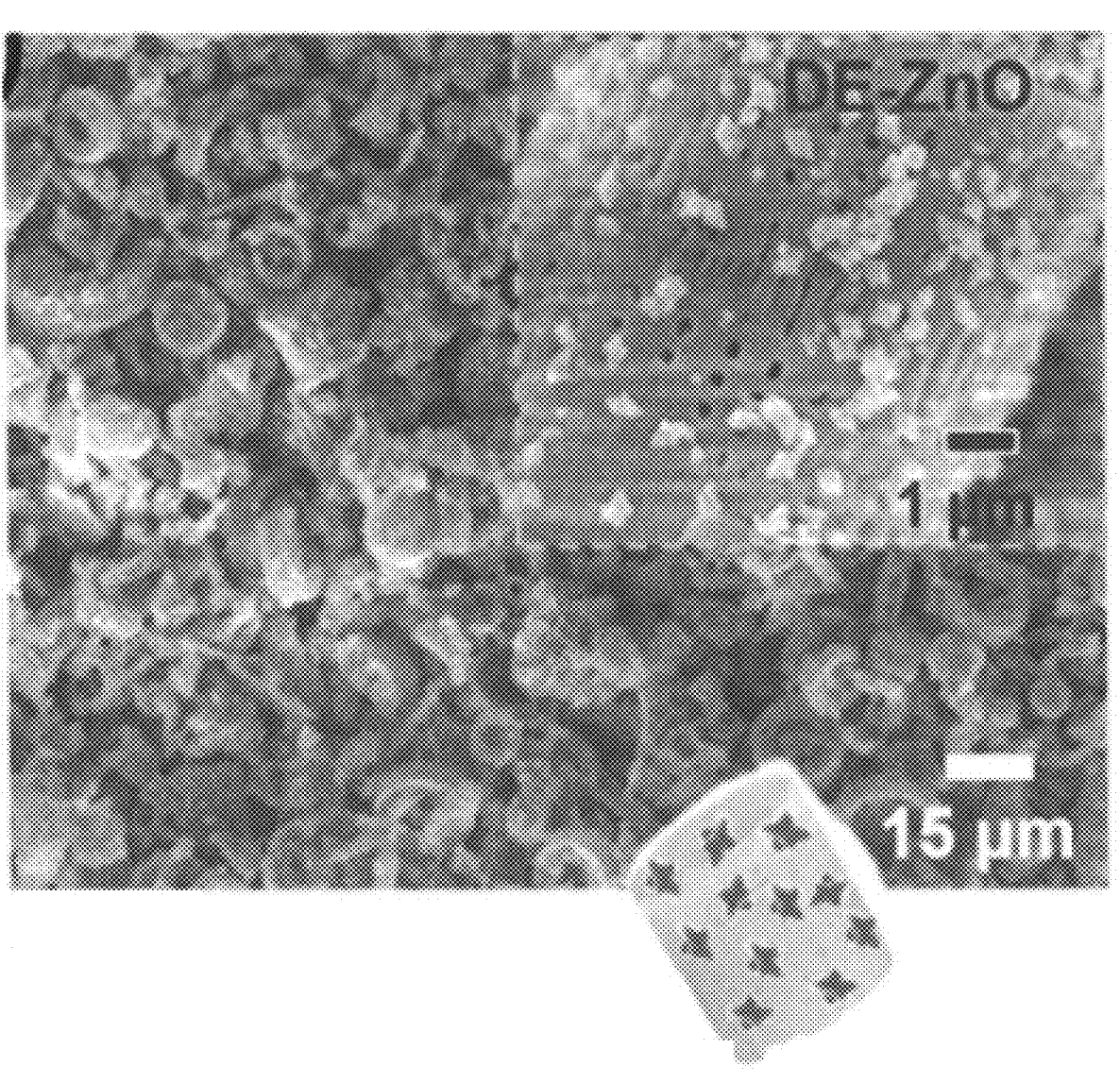
FIG. 2B is an SEM image of a DE-ZnO composite prepared by the present invention using the DE.

Diatomaceous earth was purified by gravity in distilled water, and uniform diatomaceous earth (0.5 g) was dissolved in 98 mL of ultrapure water (Milli-Q water). An SEM image of the porous diatomaceous earth (DE) used above is illustrated in FIG. 2A. Thereafter, 1 M $ZnNO_3 \cdot 6H_2O$ and 1 mL of 1 M CTAB were added to the DE solution. $Zn^{2+}$ was diffused by stirring at 90° C. to 500 rpm for 50 minutes, and thus adhered to the surface of diatomaceous earth by the van der Waals force. Thereafter, 2 mL of an ammonium hydroxide solution was added dropwise thereto under constant-rate stirring and constant temperature incubation conditions. A ZnO nanomaterial grew in the crystal direction, and the color of the reaction solution changed from a brick color (diatomaceous earth) to a pink-white color. Thereafter, the reaction vessel was transferred to an ice bath to stop the reaction. The resulting precipitate was collected by centrifugation and washed 3 times with ultrapure water (Milli-Q water) to wash away residual ions. ZnO not bound to diatomaceous earth was removed using gravity precipitation. Finally, the precipitate was dried in an oven at 56° C. overnight. An SEM image of the diatomaceous earth-ZnO composite (DE-ZnO) thus obtained is illustrated in FIG. 2B. From FIG. 2B, it can be confirmed that ZnO (approximately 300 nm in size) is uniformly distributed on the surface of diatomaceous earth.

(3) Optimization of Reaction Ratio Between DE and ZnO in DE-ZnO Composite

Experiments were performed at reaction ratios of ZnO:DE=0.25:1; 0.5:1; 1:1; 2:1; 3:1; and 4:1 to optimize the reaction ratio between ZnO and DE.

Figure 3A:
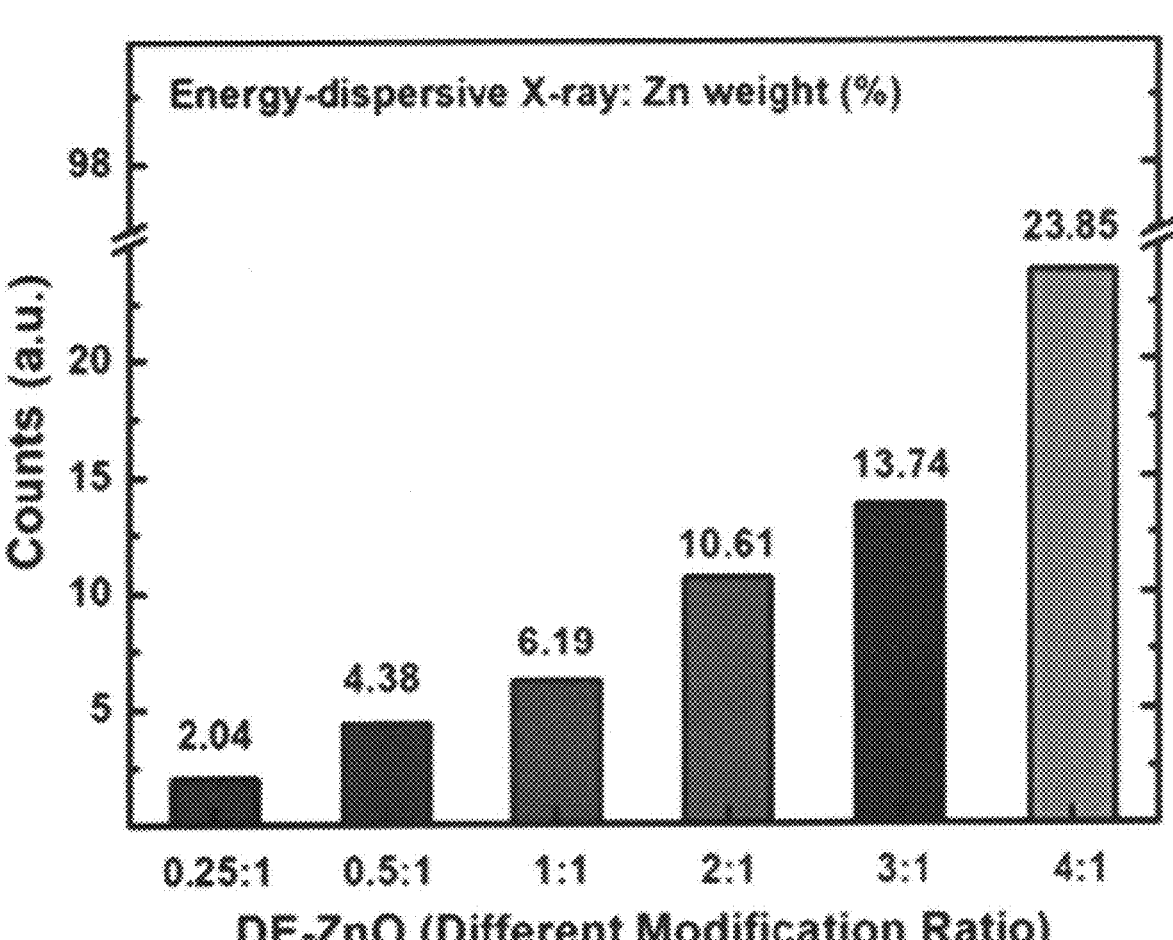
FIG. 3A illustrates the energy dispersive X-ray results of DE-ZnO.

The energy dispersive X-ray results of the DE-ZnO composite are illustrated in FIG. 3A, which shows that the percentage of ZnO on DE is 2.04%, 4.38%, 6.19%, 10.61%, 13.74%, and 23.85% (wt %), respectively, according to each reaction ratio (0.25, 0.5, 1, 2, 3, and 4).

Figure 3B:
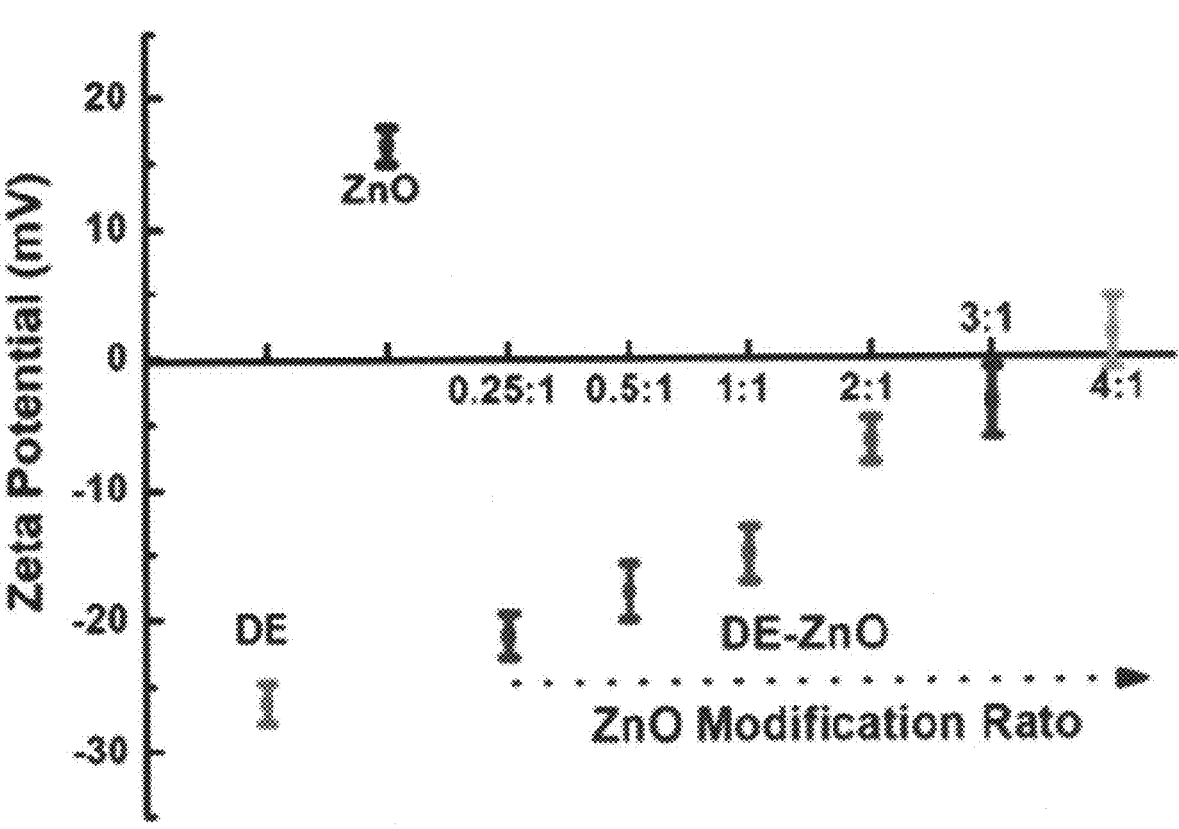
FIG. 3B illustrates the zeta potential of the DE-ZnO composite.

The zeta potential of the DE-ZnO composite is illustrated in FIG. 3B. From FIG. 3B, it could be confirmed that the surface charge of DE-ZnO is positive and has a positive correlation with the total amount of coated ZnO—S.

When the amount of synthetic ZnO—S exhibiting a positive surface charge is increased on well-washed diatomaceous earth (DE) showing a negative surface charge, a significant abundance of positive charges around the DE-ZnO composite may appear.

[Test Example 1] Evaluation of Antibacterial Activity and Cytotoxicity

Figure 4A:
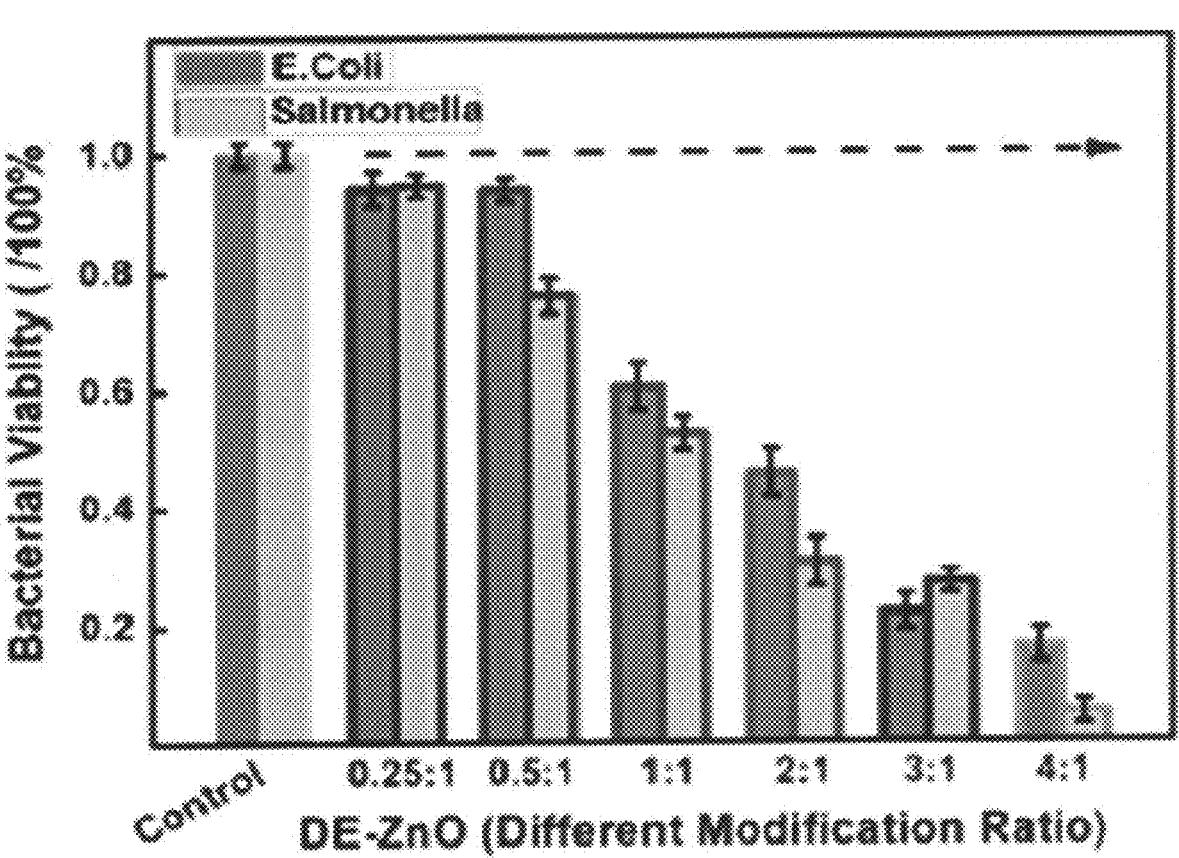
FIG. 4A is a graph of testing the antibacterial efficacy against Gram-negative bacteria (*E. coli*, *S. enterica*)
Figure 4B:
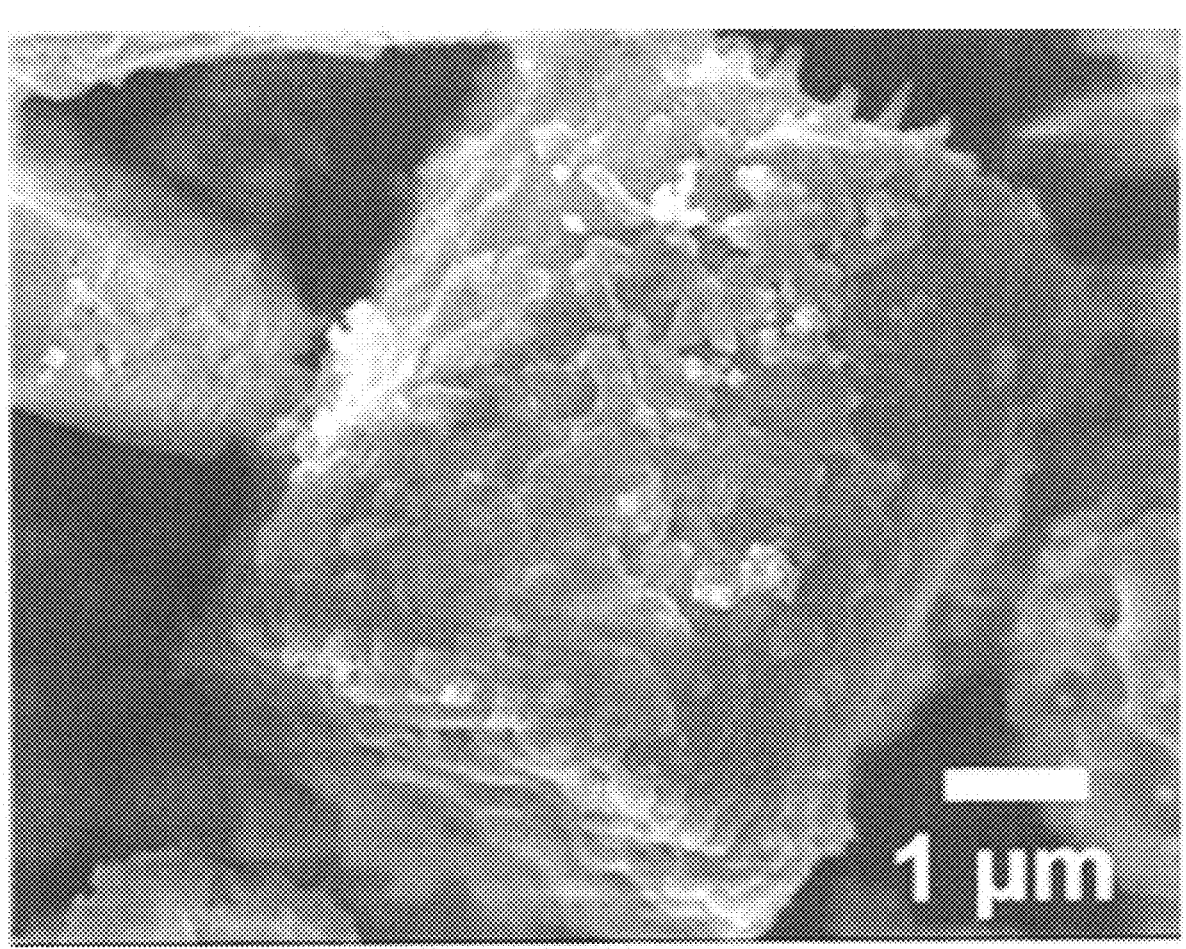
FIG. 4B is an SEM image showing the surface of the DE-ZnO composite after contact with pathogens.

*Escherichia coli* (*E. coli*) and *Salmonella enterica* (*S. enterica*) suspensions were used as Gram-negative bacteria to investigate the antibacterial effect on Gram-negative bacteria, and antibacterial activity was measured using 10 μg/mL DE-ZnO at multiple reaction ratios. For this purpose, a 10 μg/mL DE-ZnO composite was added to a tube including 0.1 mL of a $1 \times 10^7$ CFU/mL bacterial suspension and 2 mL of a LB medium. After a constant temperature incubation was performed at 37° C. for 16 hours while shaking the tube at 210 rpm, bacterial viability was confirmed by measuring the optical density of each sample at an OD of 600 nm. As illustrated in FIG. 4A, the highest antibacterial activity was shown against both *Escherichia coli* and *Salmonella* when the ratio of ZnO:DE was 4:1, and as the ZnO proportion in the DE-ZnO composite increased, the higher antibacterial properties became even higher. FIG. 4B shows that the DE-ZnO composite is able to completely absorb bacteria by destroying a bacterial cell membrane to the smallest extent.

Figure 4C:
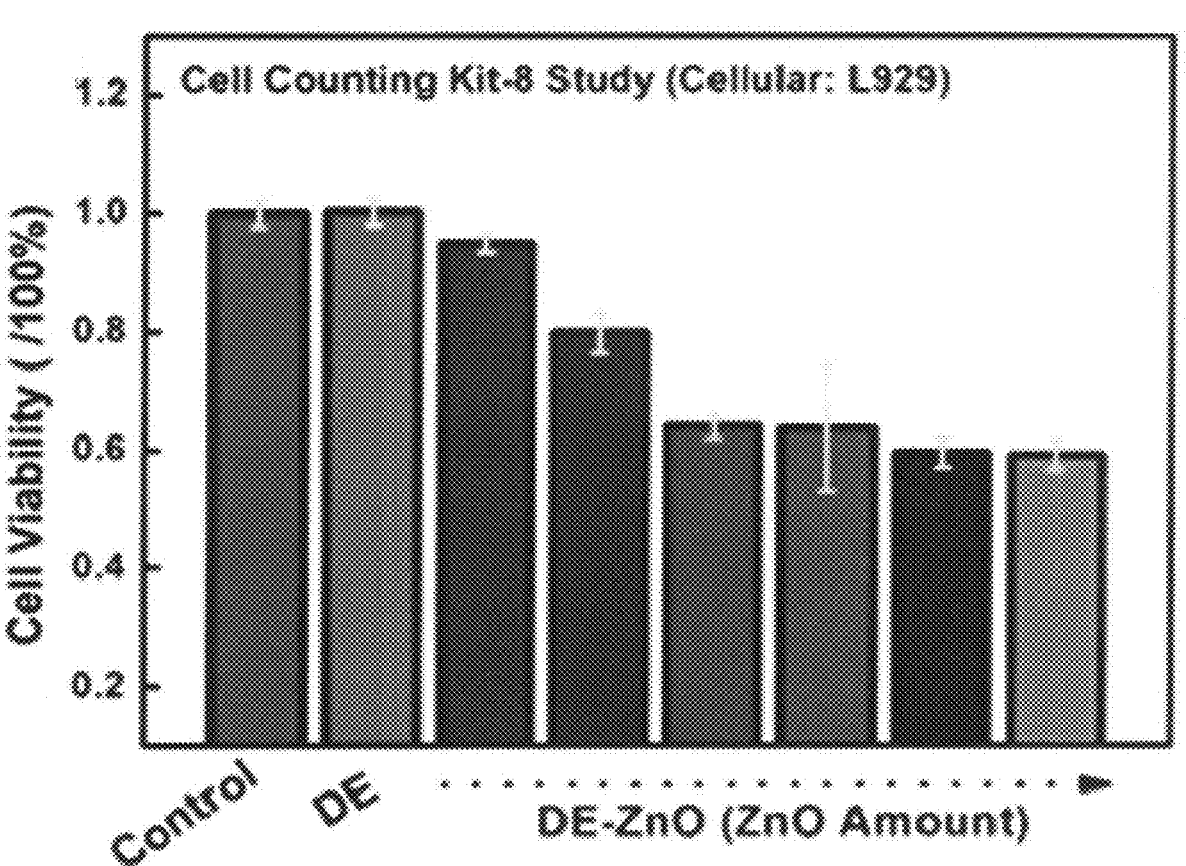
FIG. 4C illustrates the results of performing an experiment on the cytotoxicity of DE-ZnO.
Figure 4D:
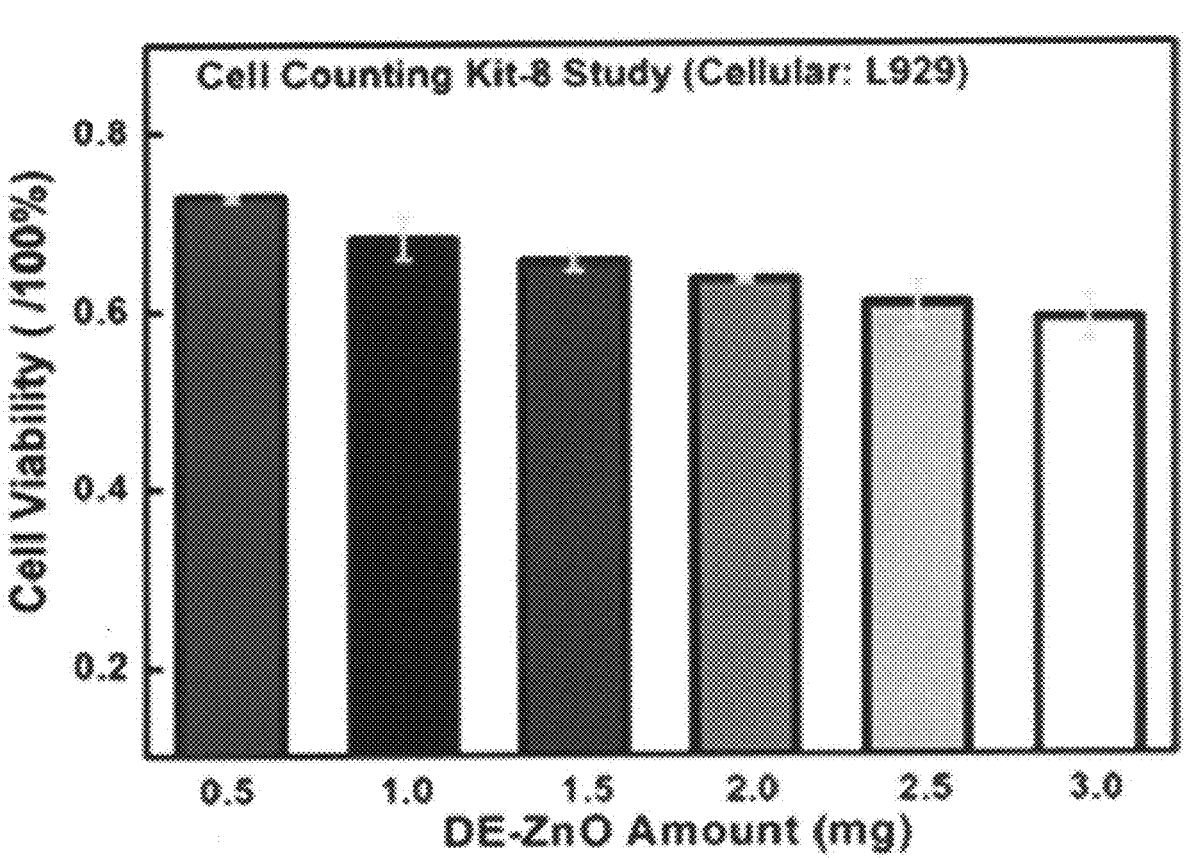
FIG. 4D illustrates the results of performing an experiment on the cytotoxicity according to the volume of DE-ZnO.

The cytotoxicity of the composite of the present invention was measured using a colorimetric analysis kit (Cell Counting Kit-8). The cytotoxicity of the DE-ZnO composite was measured at a volume of 0.25 mg while varying the reaction ratio (ZnO:DE=0.25:1, 0.5:1, 1:1, 2:1, 3:1, and 4:1), and the results are illustrated in FIG. 4C. Thereafter, to examine cytotoxicity according to the dose, in 96-well microplates, DE-ZnO (ZnO:DE=2:1) samples at a concentration of 0.5, 1.0, 1.5, 2.0, 2.5 and 3.0 mg (in DMEM) were applied to adherent L929 cells (non-cancerous), and the results are illustrated in FIG. 4D. L929 cell viability at 3 mg or less of the DE-ZnO complex was relatively stable (70 to 60%), indicating excellent biocompatibility.

[Test Example 2] Evaluation of Antifungal Activity

Figure 5A:
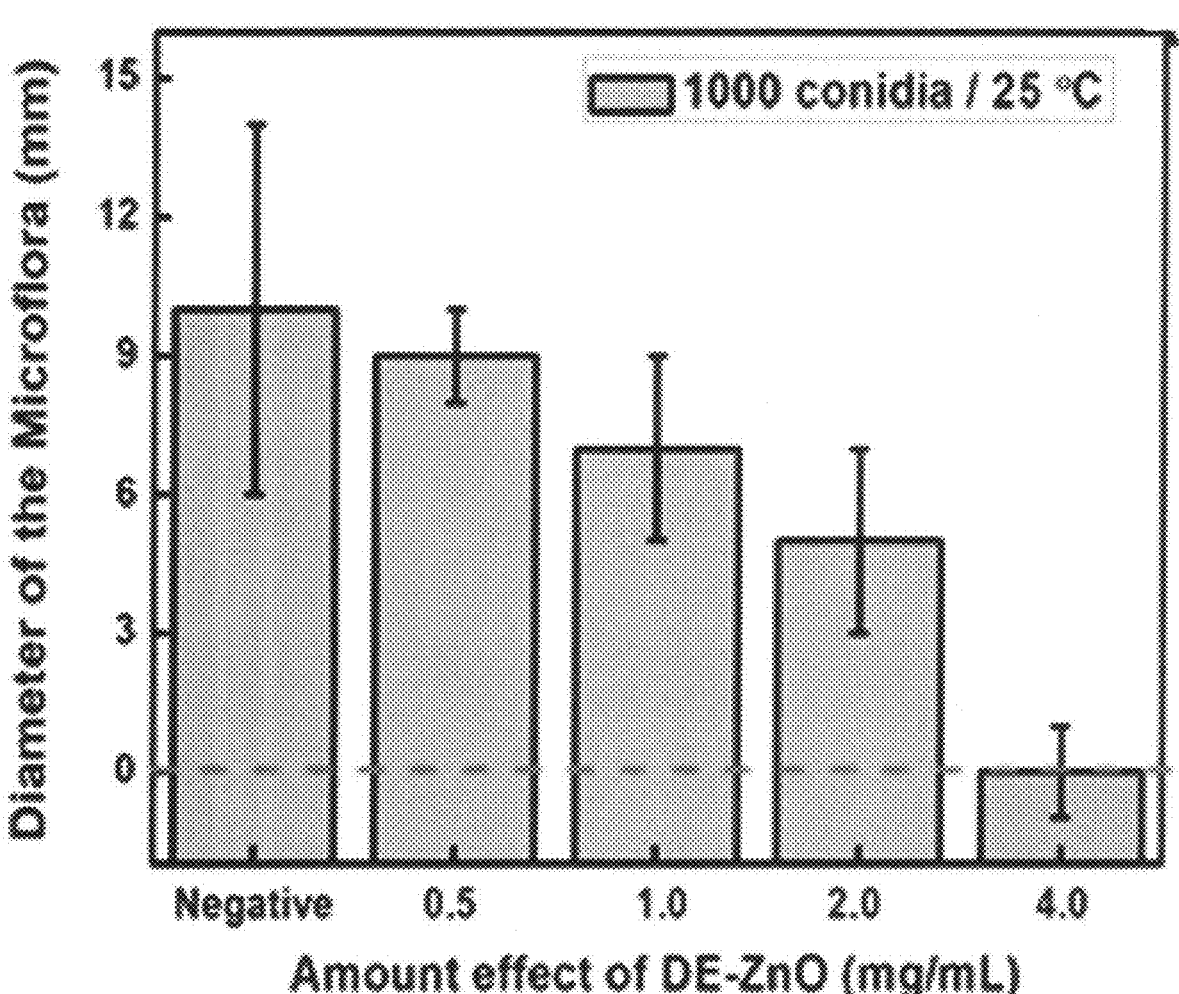
FIG. 5A illustrates the experimental results investigating an effect of the amount of DE-ZnO composite on antifungal activity (1000 conidia, 25° C., 3-day culture)

To confirm the antifungal activity of the composite of the present invention, *Aspergillus fumigatus* (10000 conidia, 25° C.) was used, and DE-ZnO (ZnO:DE=2:1, 10.61% ZnO) at a concentration of 0.5, 1.0, 2.0 and 4.0 mg/mL was mixed with the inoculated *Aspergillus* to incubate the mixture. The growth state of the mold was monitored for 14 days, the growth photographs of mold were recorded every 12 hours, and growth areas were measured with Image-J. The diameters of the radial microflora on day 7 was measured, and are illustrated in FIG. 5A. It can be confirmed that the mold hardly grows at a concentration of 4.0 mg/mL of the composite. This indicates that the DE-ZnO composite kills mold activity by not only inhibiting mold growth, but also destroying the mold cell wall.

Figure 5B:
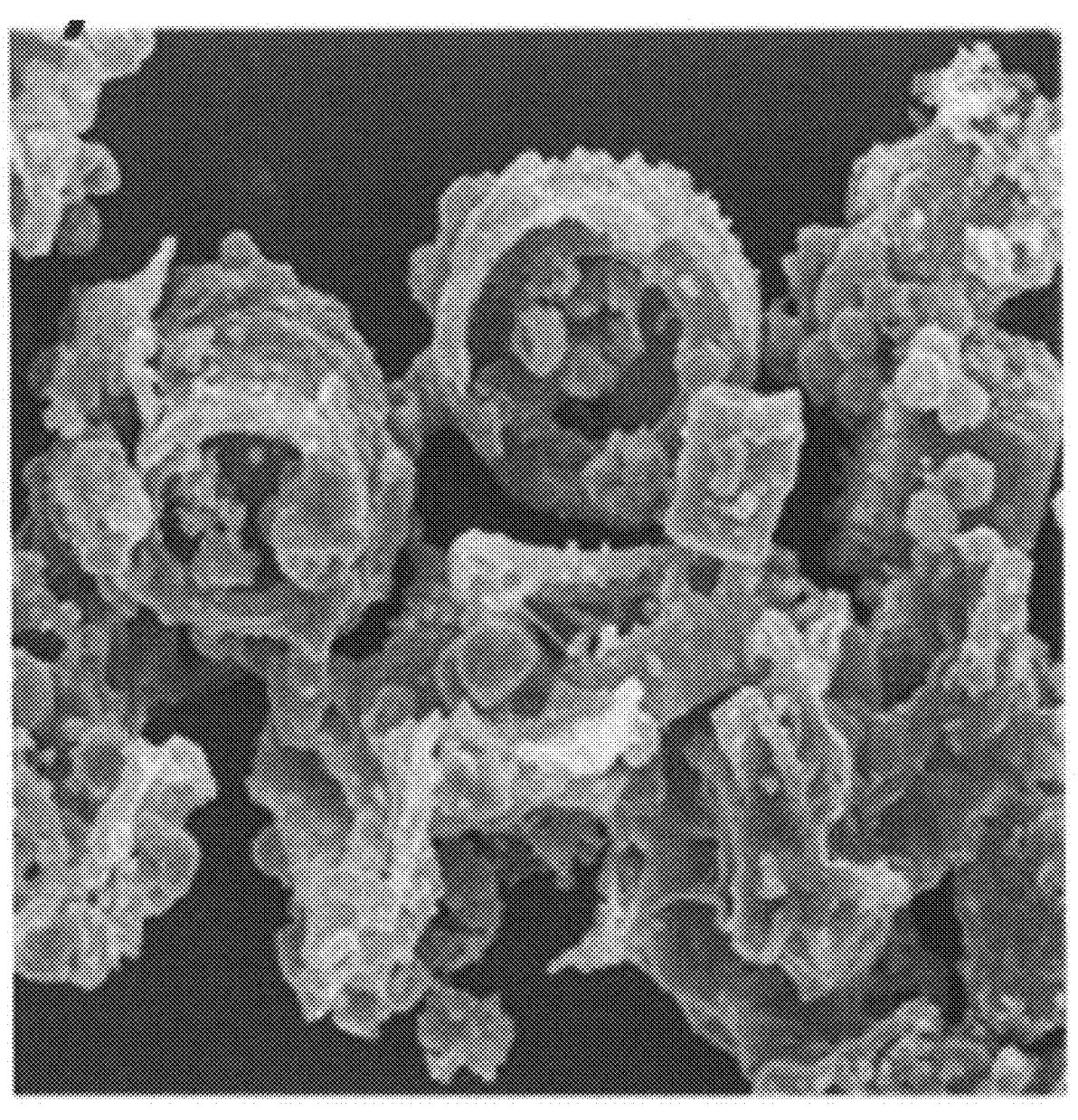
FIG. 5B is an SEM image of the mold *Aspergillus* absorbed on the DE-ZnO composite.

As additional experiments, the DE-ZnO composite was added to a mold spore solution for 3 minutes. An SEM image of the mold *Aspergillus* absorbed on the DE-ZnO composite is illustrated in FIG. 5B. As illustrated in FIG. 5B, DE-ZnO absorbed mold spores well, which is due to the capture enrichment property of the DE-ZnO composite, and the corresponding property becomes an important advantage for antifungal activity.

When the antifungal activity of the DE-ZnO composite is summarized from the above results, it can be understood that first, a capture-enrich step between the cell wall of the mold and the active surface of the DE-ZnO composite is achieved by the surface charge adsorption and the van der Waals force, and second, the cell membrane of mold is destroyed and lysed as a nano-lysis step of DE-ZnO.

[Test Example 3] Combination Experiment with Other Antibiotics

Figure 6A:
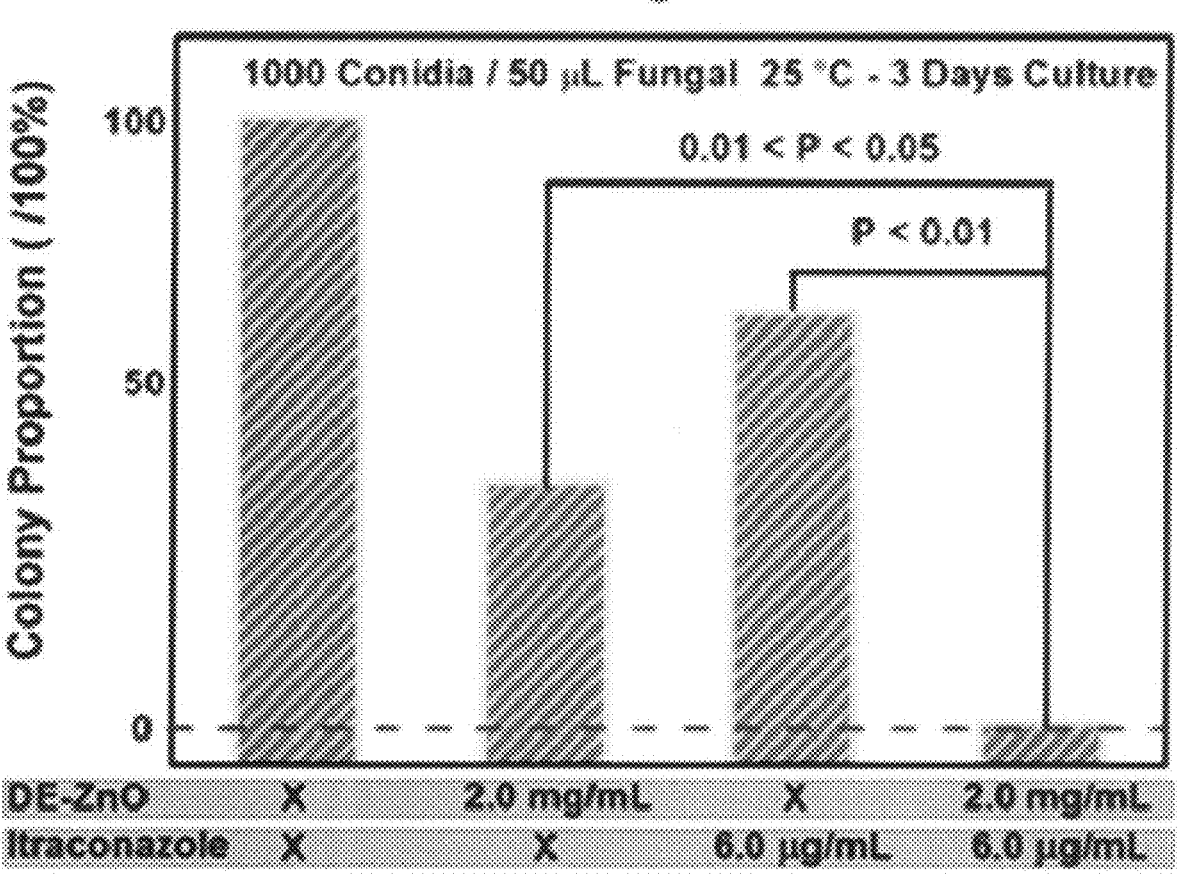
FIG. 6A illustrates the antifungal activity of the DE-ZnO composite, itraconazole, and a DE-ZnO and itraconazole combination group (day 3 of culture, 1000 conidia)
Figure 6B:
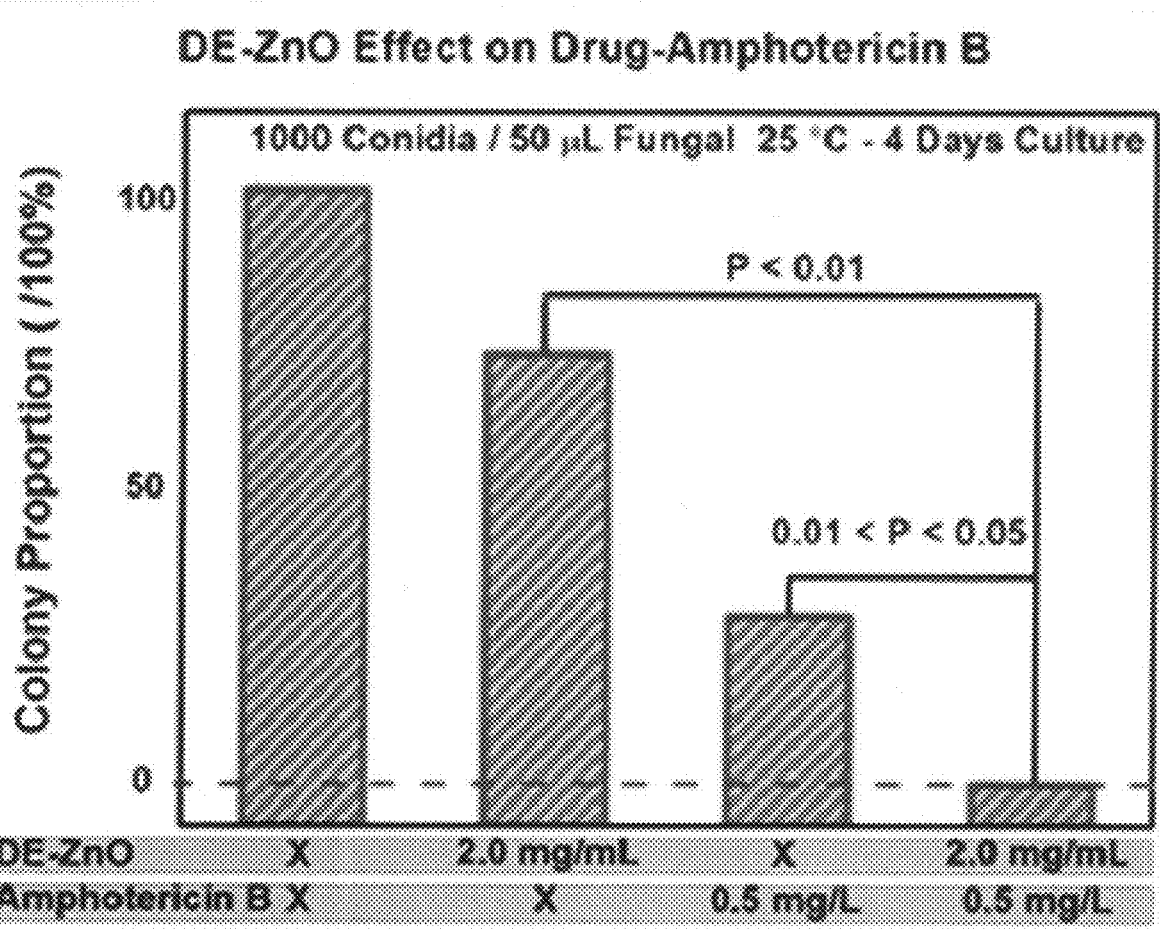
FIG. 6B illustrates the antifungal activity of the DE-ZnO composite, amphotericin B, and a combination group of the DE-ZnO composite and amphotericin B (day 4 of culture, 1000 spores)

Experiments were conducted to confirm the effect of the combined use of commercially available antibiotics (amphotericin B and itraconazole) and the composite of the present invention. 6.0 μg/mL itraconazole or 0.5 mg/L amphotericin B and a 2.0 mg/mL DE-ZnO composite were used as initial concentrations. FIG. 6A illustrates each effect of single use and combined use of DE-ZnO and itraconazole, FIG. 6B illustrates each effect of single use and combined use of DE-ZnO and amphotericin B, and the synergistic effect according to the combined use can be confirmed. That is, as seen in the combination result of itraconazole and DE-ZnO and the combination result of amphotericin B and DE-ZnO, it can be seen that the DE-ZnO structure improves the effect of existing antibiotics.

Figure 6C:
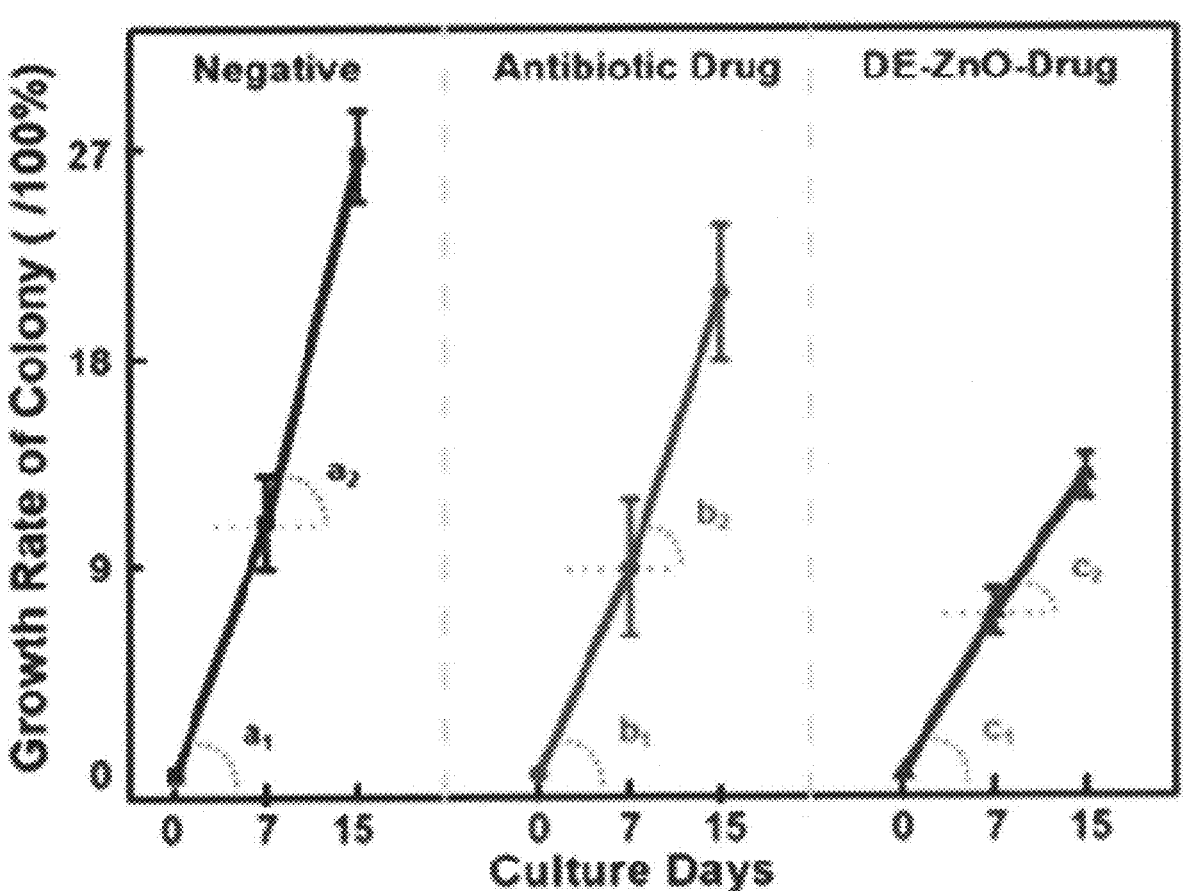
FIG. 6C is a graph showing the growth rate of colony during long-term culture (15 days)

FIG. 6C is a graph showing the growth rate of mold colonies in the control, the antibiotic alone administration group, and the antibiotic and DE-ZnO combination administration group. From the graph slope "a1>b1>c1", it can be seen that the DE-ZnO composite improves the antifungal activity of antibiotics. In addition, from the graph slope "a2>a1; b2>b1" after day 7, mold growth became faster in the control and the antibiotic alone group after day 7, and in contrast, from the point that "c2<c1", it can be seen that the DE-ZnO composite and antibiotic combination administration group exhibits a strong inhibitory effect for a long period of time.

Figure 6D:
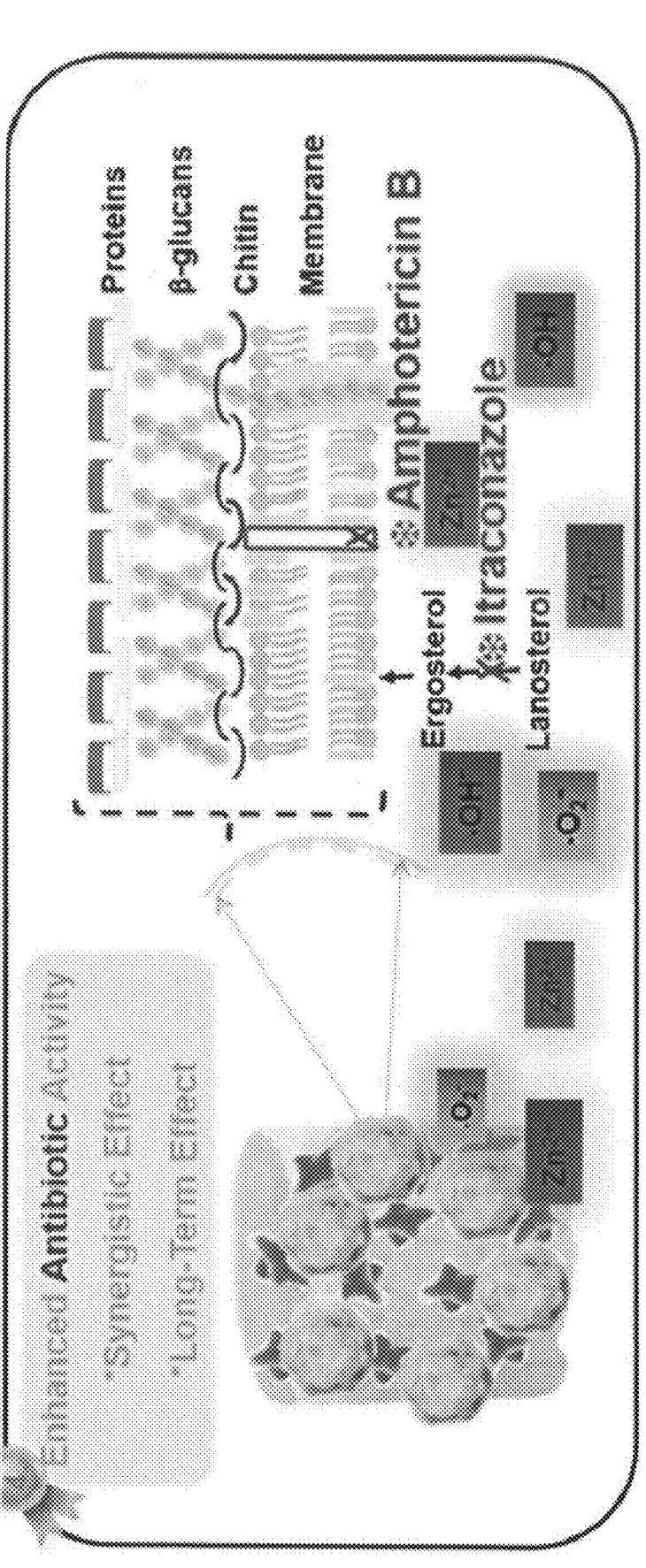
FIG. 6D is a schematic view explaining synergistic effects exhibited by the combined use of DE-ZnO and existing antibiotics.
Figure 7A:
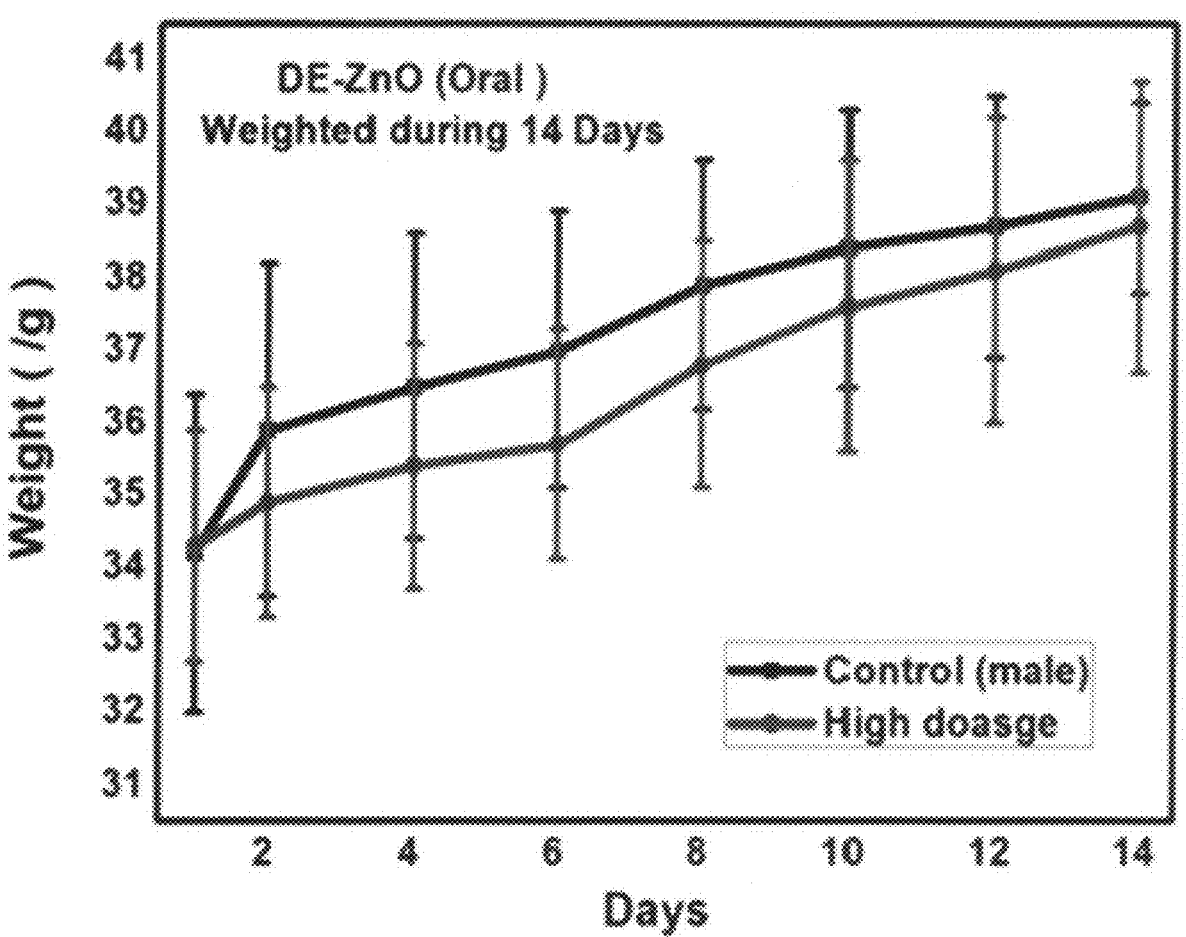
FIGS. 7A and 7B illustrate the results of observing the body weights of male and female mice for 14 days, respectively.
Figure 7B:
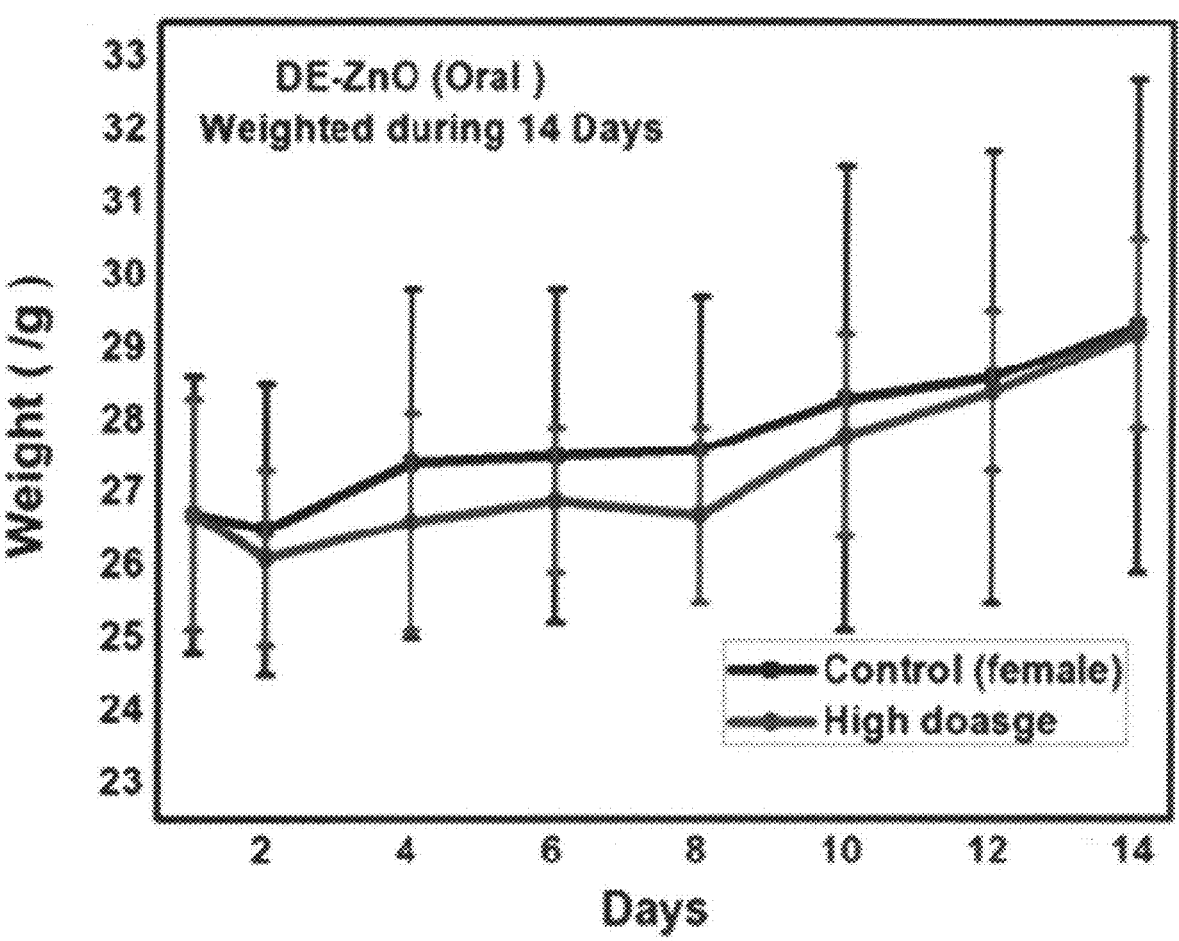
Figure 7C:
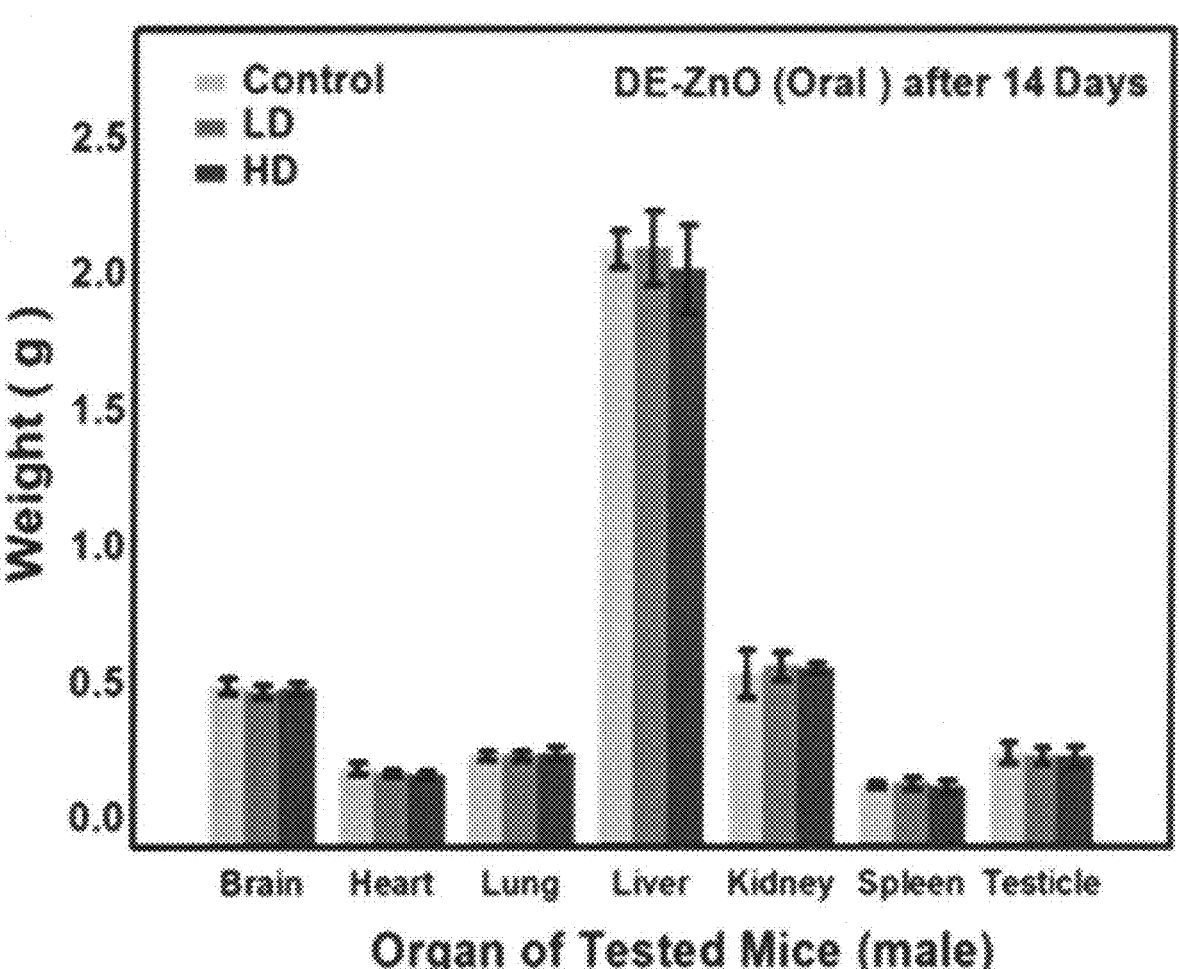
FIGS. 7C and 7D illustrate long-term weight changes of mice after 14 days of oral administration.
Figure 7D:
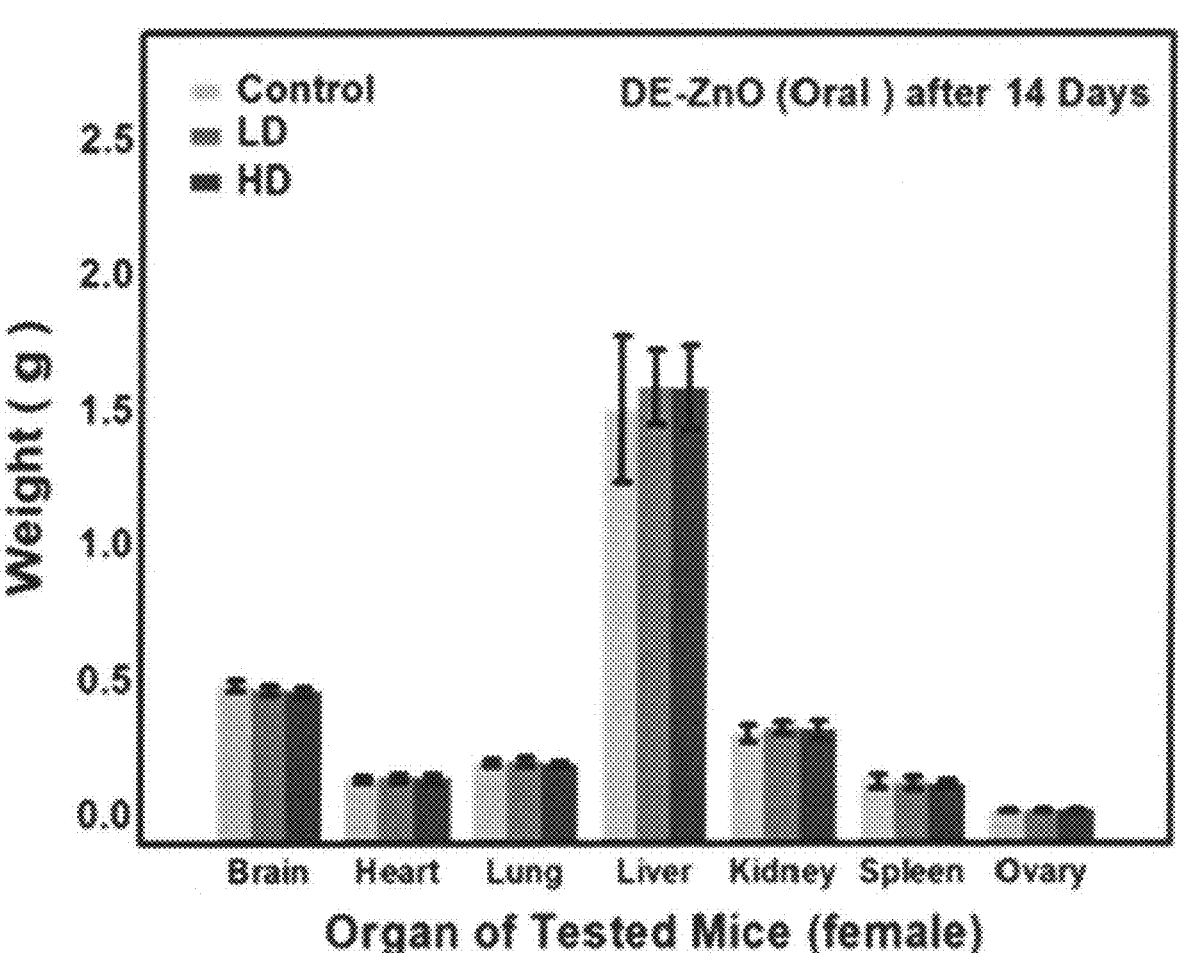

FIG. 6D is a schematic view describing the synergistic effect exhibited by the combined use of DE-ZnO and existing antibiotics, and it is understood that the aforementioned long-term effect is due to the delayed release of ions and ROS.

[Test Example 4] In Vivo Experiment-Toxicity Test

For toxicity testing, the mice consisted of a normal control for oral administration and a DE-ZnO oral administration group with a dose of 2 mg/kg (low dose, LD) and a dose of 10 mg/kg (high dose, HD) for each of males and females. General symptoms were observed for 6 hours after administration of the test substance, general symptoms were observed once daily for 14 days before the date of autopsy, and the animals were weighed 3 times a week. After blood was collected from the abdominal vein by opening the abdomen on the final day of the test, the organs were visually observed, the organ weights were measured by removing the brain, the heart, the lungs, the liver, the spleen, the kidneys and the testicles/the ovaries, and the results are illustrated in FIGS. 7A to 7D. Referring to FIGS. 7A to 7D, as a result of the experiment, no cases of death were observed in the test substance-administered groups at all doses during the observation period. In conclusion, as a result of a single oral administration of DE-ZnO to ICR mice at a dose of 2 mg/kg or a dose of 10 mg/kg under the conditions of the present test, no toxicity was observed, and it is determined that the approximate lethal dose exceeded 10 mg/kg for both males and females.

Although the present invention has been described above with reference to preferred exemplary embodiments of the present invention, a person with ordinary skill in the art can understand that the present invention can be modified and changed in various ways in a range not departing from the spirit and scope of the present invention described in the following claims.

What is claimed is:

1. An antibiotic composition comprising, as an active ingredient, a diatomaceous earth-zinc oxide composite comprising zinc oxide on diatomaceous earth, wherein the antibiotic composition is configured for oral administration, and wherein the zinc oxide is a nanocrystal having a plurality of sharp protrusions arranged in an annular pattern.

2. The antibiotic composition of claim 1, wherein the zinc oxide is a nanocrystal synthesized and grown by hydrothermal synthesis on diatomaceous earth.

3. The antibiotic composition of claim 1, wherein the zinc oxide is a nanocrystal having an average diameter of 200 to 400 nm.

4. The antibiotic composition of claim 1, wherein the diatomaceous earth-zinc oxide composite exhibits a positive surface charge.

5. The antibiotic composition of claim 1, wherein the zinc oxide in the diatomaceous earth-zinc oxide composite is comprised at a reaction ratio of 1 or more with respect to the diatomaceous earth.

6. The antibiotic composition of claim 5, wherein a reaction ratio of the zinc oxide to the diatomaceous earth is in a range of 1:1 to 4:1.

7. The antibiotic composition of claim 1, wherein the antibiotic composition has antiviral, antibacterial or antifungal activity.

8. The antibiotic composition of claim 7, wherein the antibiotic composition has antibacterial activity against Gram-negative bacteria.

9. The antibiotic composition of claim 8, wherein the antibiotic composition has antibacterial activity against *Escherichia coli* or *Salmonella.*

10. The antibiotic composition of claim 7, wherein the antibiotic composition has antifungal activity against fungi of the genus *Aspergillus.*

11. A method of (1) treating infections by viruses, bacteria, or fungi, or (2) inhibiting the growth of fungi, the method comprising the step of orally administering the antibiotic composition of claim 1 to a subject in need thereof.

12. An antifungal combination preparation comprising the antibiotic composition of claim 1 and an antifungal agent.

13. The antifungal combination preparation of claim 12, wherein the antifungal agent is itraconazole or amphotericin B.

14. A method of increasing antifungal activity of an antifungal agent, comprising steps of:

administering the antibiotic composition according to claim 1 to a subject in need thereof; and administering the antifungal agent to a subject in need thereof.

15. The method according to claim 14, wherein the antifungal agent comprises itraconazole or amphotericin B.

* * * * *